US012788946B2

(12) United States Patent
Ma et al.

(10) Patent No.: US 12,788,946 B2
(45) Date of Patent: Nov. 10, 2026

(54) METHOD OF REPOSITIONING A CATHETER DISTAL TIP AND RELATED SYSTEMS

(71) Applicant: Becton, Dickinson and Company, Franklin Lakes, NJ (US)

(72) Inventors: Yiping Ma, Layton, UT (US); Jonathan Karl Burkholz, Salt Lake City, UT (US); John Lackey, West Valley City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 866 days.

(21) Appl. No.: 17/825,499

(22) Filed: May 26, 2022

(65) Prior Publication Data

US 2022/0379090 A1 Dec. 1, 2022

Related U.S. Application Data

(60) Provisional application No. 63/194,067, filed on May 27, 2021.

(51) Int. Cl.
*A61M 25/01* (2006.01)
*A61M 39/10* (2006.01)

(52) U.S. Cl.
CPC .... *A61M 25/0127* (2013.01); *A61M 25/0108* (2013.01); *A61M 39/10* (2013.01); *A61M 2039/1077* (2013.01); *A61M 2205/36* (2013.01)

(58) Field of Classification Search
CPC .......... A61M 25/0127; A61M 25/0158; A61M 2025/0166; A61B 34/73; A61B 2034/731; A61B 2034/733
See application file for complete search history.

(56) References Cited

U.S. PATENT DOCUMENTS

| | | | | | |
|---|---|---|---|---|---|
| 4,063,561 | A * | 12/1977 | McKenna | A61M 16/04 128/207.15 |
| 4,809,713 | A | 3/1989 | Grayzel | |
| 5,156,911 | A | 10/1992 | Stewart | |
| 5,843,153 | A * | 12/1998 | Johnston | A61B 34/73 600/585 |
| 6,524,303 | B1 | 2/2003 | Garibaldi | |
| 10,383,595 | B2 | 8/2019 | Tropello | |

(Continued)

FOREIGN PATENT DOCUMENTS

| | | | |
|---|---|---|---|
| CN | 110665123 | A | 1/2020 |
| JP | 2019521743 | A | 8/2019 |

*Primary Examiner* — Kami A Bosworth
(74) *Attorney, Agent, or Firm* — The Webb Law Firm

(57) ABSTRACT

A catheter assembly may include a catheter adapter, which may include a distal end, a proximal end, and a lumen extending through the distal end and the proximal end of the catheter adapter. The catheter assembly may also include a catheter extending from the distal end of the catheter adapter. The distal tip of the catheter may include a magnetic material. A method of repositioning the distal tip of the catheter may include inserting the distal tip of the catheter into a blood vessel. The method may include attaching another magnetic material to skin, and the distal tip of the catheter may move toward the other magnetic material. At least one of the magnetic material and the other magnetic material may include a magnet. A kit may include the catheter assembly and/or the other magnetic material.

14 Claims, 6 Drawing Sheets

(56) References Cited

U.S. PATENT DOCUMENTS

| | | | | |
|---|---|---|---|---|
| 10,406,358 | B1 * | 9/2019 | Bertoch | A61N 1/30 |
| 2002/0019644 | A1 * | 2/2002 | Hastings | A61B 17/320758 606/41 |
| 2003/0154986 | A1 * | 8/2003 | Fariss | A61J 15/0096 128/207.14 |
| 2005/0161052 | A1 | 7/2005 | Rezai et al. | |
| 2007/0123964 | A1 | 5/2007 | Davies et al. | |
| 2010/0105984 | A1 * | 4/2010 | Brewer | A61M 25/0127 600/118 |
| 2010/0145147 | A1 | 6/2010 | Pinsky et al. | |
| 2011/0087223 | A1 * | 4/2011 | Spivey | A61B 18/14 606/49 |
| 2011/0295108 | A1 * | 12/2011 | Cox | A61B 5/06 600/424 |
| 2015/0202408 | A1 * | 7/2015 | McMurtry | A61M 25/01 604/95.01 |
| 2017/0252539 | A1 * | 9/2017 | Hansen | A61B 34/73 |
| 2017/0348509 | A1 * | 12/2017 | Burkholz | A61M 25/0618 |
| 2018/0333559 | A1 * | 11/2018 | Makey | A61B 34/73 |
| 2018/0361115 | A1 * | 12/2018 | Demertzis | A61M 25/0127 |
| 2019/0000306 | A1 * | 1/2019 | Tozzi | A61B 1/00158 |
| 2019/0053938 | A1 * | 2/2019 | Mandal | A61F 7/007 |
| 2019/0224390 | A1 | 7/2019 | Barry | |
| 2019/0282783 | A1 * | 9/2019 | De Cicco | A61B 5/062 |
| 2020/0230361 | A1 * | 7/2020 | Nelson | A61M 25/0043 |
| 2021/0244482 | A1 * | 8/2021 | Tropello | A61J 15/0003 |
| 2021/0275766 | A1 * | 9/2021 | Tropello | A61M 16/0472 |

* cited by examiner

METHOD OF REPOSITIONING A CATHETER DISTAL TIP AND RELATED SYSTEMS

CROSS-REFERENCE TO RELATED APPLICATION

The present application claims priority to United States Provisional Application Ser. No. 63/194,067, entitled "Method of Repositioning a Catheter Distal Tip and Related Systems", filed May 27, 2021, the entire disclosure of which is hereby incorporated by reference in its entirety.

BACKGROUND OF THE INVENTION

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of intravenous (IV) catheter device includes a catheter that is over-the-needle. As its name implies, the catheter that is over-the-needle may be mounted over an introducer needle having a sharp distal tip. The IV catheter device may include a catheter adapter, the catheter extending distally from the catheter adapter, and the introducer needle extending through the catheter. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Infusion and blood withdrawal using the catheter may be difficult for several reasons, particularly when an indwelling time of the catheter increases. A thrombus may form within the vasculature near the distal tip of the catheter. The thrombus may partially or completely block or a fluid pathway through the catheter, which may impair fluid infusion and/or collection of a high-quality blood sample.

The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to vascular access devices, as well as related systems and methods. More particularly, in some embodiments, the present disclosure relates to a method of repositioning a distal tip of a catheter, as well as related devices and systems. In some embodiments, the method of repositioning the distal tip of the catheter may include inserting the distal tip of the catheter of a catheter assembly into a blood vessel. In some embodiments, the distal tip of the catheter may include a magnetic material. In some embodiments, the method may include attaching another magnetic material to skin. In some embodiments, the distal tip of the catheter may move toward the other magnetic material. In some embodiments, at least one of the magnetic material and the other magnetic material may include a permanent magnet or an electromagnet.

In some embodiments, the catheter assembly may include a catheter adapter. In some embodiments, the catheter adapter may include a distal end, a proximal end, and a lumen extending through the distal end and the proximal end. In some embodiments, the catheter may extend from the distal end of the catheter adapter. In some embodiments, the catheter may include a peripheral intravenous catheter, a midline catheter, or a peripherally-inserted central catheter.

In some embodiments, the distal tip of the catheter of the catheter assembly may be inserted into the blood vessel such that the distal tip contacts a wall of the blood vessel. In some embodiments, attaching the other magnetic material to the skin may include attaching an adhesive patch to the skin. In some embodiments, the other magnetic material may be coupled to the adhesive patch. In some embodiments, the adhesive patch may be coupled to a heating element.

In some embodiments, attaching the other magnetic material to the skin may include placing an arm band around the skin. In some embodiments, the other magnetic material may be coupled to the arm band. In some embodiments, the method may include rotating the arm band with respect to the skin such that a position of the other magnetic material is changed with respect to the distal tip.

In some embodiments, the other magnetic material may be attached to the skin after the distal tip of the catheter is inserted into the blood vessel. In some embodiments, the other magnetic material may be attached to the skin such that the other magnetic material is aligned with a longitudinal axis of the catheter. In some embodiments, the other magnetic material may be attached to the skin to a side of the longitudinal axis of the catheter. In some embodiments, the other magnetic material may be attached to the skin before the distal tip of the catheter is inserted into the blood vessel. In these embodiments, the distal tip of the catheter may be inserted into the blood vessel such that the other magnetic material is aligned with the longitudinal axis of the catheter or disposed to a side of the longitudinal axis of the catheter.

In some embodiments, the catheter may include one or more strips extending longitudinally within the catheter and embedded within the catheter. In some embodiments, the strips may include a radiopaque material and the magnetic material.

In some embodiments, the magnetic material may be embedded in the distal tip of the catheter. In some embodiments, the magnetic material may include an annular ring embedded within the distal tip of the catheter. In some embodiments, the magnetic material and/or the other magnetic material may include an electromagnet. In some embodiments, the magnetic material and/or the other magnetic material may include a permanent magnet.

In some embodiments, a kit may include the catheter assembly and/or the other magnetic material. In some embodiments, in response to attaching the other magnetic material to skin and inserting the distal tip of the catheter into a blood vessel, the distal tip of the catheter may be configured to move towards the other magnetic material. In some embodiments, the kit may include the adhesive patch and/or the arm band, which may be coupled to the other magnetic material. In some embodiments, the kit may include another means to attach the other magnetic material to the skin.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DETAILED DESCRIPTION OF THE INVENTION

Figure 1A:
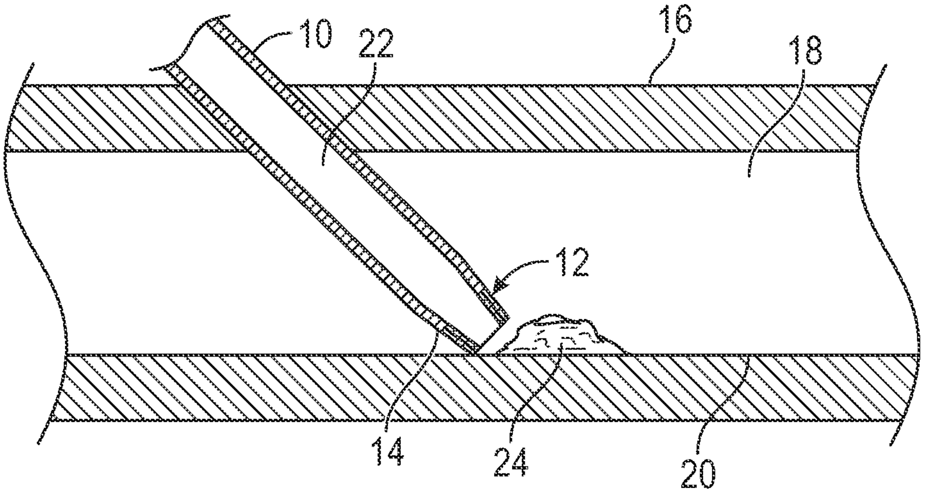
FIG. 1A is a longitudinal cross-sectional view illustrating an example catheter inserted into an example blood vessel, according to some embodiments.
Figure 1B:
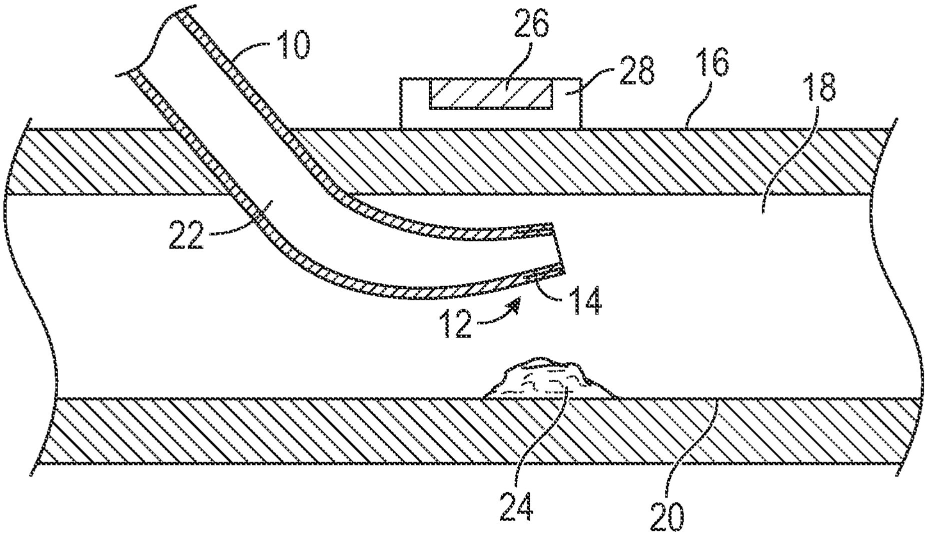
FIG. 1B is a longitudinal cross-sectional view illustrating an example distal tip of the catheter of FIG. 1A that has been repositioned, according to some embodiments.

Referring now to FIGS. 1A-1B, a catheter 10 is illustrated, according to some embodiments. In some embodiments, the catheter 10 may include a distal tip 12, which may be include a magnetic material 14. In some embodiments, the distal tip 12 may be inserted through skin 16 of a patient and into a blood vessel 18 or vein. In some embodiments, an introducer needle (not illustrated) having a sharp distal tip may extend through the catheter 10 to facilitate insertion of the catheter 10 through the skin 16 and into the blood vessel 18. In some embodiments, the introducer needle may be removed in response to the distal tip 12 being inserted into the blood vessel 18. In some embodiments, the introducer needle and the catheter 10 may be inserted through the skin 16 at approximately a 45° angle with respect to the skin 16. In some embodiments, the catheter 10 may be used for blood collection and/or fluid infusion after being placed within the blood vessel 18 and removal of the introducer needle.

In some embodiments, the distal tip 12 of the catheter 10 may be inserted into the blood vessel 18 such that the distal tip 12 contacts a wall 20 of the blood vessel 18. In some instances, the distal tip 12 may rest or rub on the wall 20. In some embodiments, in response to the catheter 10 being inserted into the blood vessel 18 for a prolonged period of time and/or contacting the wall 20 of the blood vessel 18, a thrombus 24 may form, which may partially or completely block fluid from entering a fluid pathway 22 of the catheter 10, as illustrated, for example, in FIG. 1A. In some instances, the thrombus 24 may occlude the blood vessel 18 under vacuum pressure applied during blood collection through the catheter 10.

In some embodiments, the distal tip 12 may be configured to be repositioned, which may move the distal tip 12 away from the thrombus 24 and decrease blockage of the catheter 10. For example, the distal tip 12 may be configured to move or bend from a first position to a second position in response to attraction of the magnetic material 14 of the distal tip 12 to another magnetic material 26 on the skin 16. An example first position is illustrated in FIG. 1A, in which the catheter 10 is generally straight. In some embodiments, the first position may correspond to a position of the catheter 10 immediately after insertion into the blood vessel 18. An example second position is illustrated in FIG. 1B. In some embodiments, the other magnetic material 26 may be positioned on the skin 16 such that the distal tip 12 of the catheter 10 within the blood vessel 18 moves towards the other magnetic material 26.

In some embodiments, the other magnetic material 26 may be attached to the skin using any suitable means. For example, the other magnetic material 26 may be coupled to an adhesive patch 28, as illustrated, for example, in FIG. 1B. In some embodiments, a bottom surface of the adhesive patch 28 may include an adhesive configured to stick to the skin 16. In some embodiments, the adhesive patch 28 may facilitate securement of the other magnetic material 26 in a desired location. In some embodiments, the adhesive patch 28 may be constructed of woven fabric, plastic, latex, or another suitable material.

In some embodiments, in order to change a location of the distal tip 12 and improve fluid flow therethrough, the other magnetic material 26 may be attached to the skin 16 after the catheter 10 is inserted into the blood vessel 18 and/or is disposed within the blood vessel 18 for a particular amount of time. In some embodiments, the other magnetic material 26 may be attached to the skin 16 when an occlusion during blood draw is encountered. In some embodiments, the other magnetic material 26 may be attached to the skin 16 during an entirety of a dwell period of the catheter 10 within the blood vessel 18. In these and other embodiments, the other magnetic material 26 may be attached to the skin prior to insertion of the catheter 10 into the blood vessel 18 such that the distal tip 12 is immediately attracted to the other magnetic material 26 when inserted into the blood vessel 18, moving the distal tip 12 away from the wall of the blood vessel 18 and preventing thrombus formation. In some embodiments, the other magnetic material 26 may be moved to one or more different positions on the skin 16 during the dwell period of the catheter 10, which may reposition the distal tip 12 away from the thrombus 24, the wall, or a potential blockage.

In some embodiments, the magnetic material 14 may include a permanent magnet, an electromagnet, or one or more materials attracted to such magnets, such as, for example, ferromagnetic materials, ferrimagnetic materials, paramagnetic materials, and the like. In some embodiments, the other magnetic material 26 may include a permanent magnet, an electromagnet, or one or more materials attracted to such magnets, such as, for example, ferromagnetic materials, ferrimagnetic materials, paramagnetic materials, and the like. In some embodiments, at least one of the magnetic material 14 and the other magnetic material 26 may include an electromagnet and a permanent magnet, such that the magnetic material 14 and the other magnetic material 26 are attracted to each other.

In some embodiments, a wall of the catheter 10 may be constructed of a material such as plastic or another suitable material. In some embodiments, the magnetic material 14 may be embedded in the distal tip 12 of the catheter 10, such as within the wall of the catheter 10. In some embodiments, when embedding the magnetic material 14 in the distal tip 12 and/or the catheter 10, portions of the magnetic material 14 may be uncovered by the material of the wall. In other embodiments and as illustrated, for example, in FIGS. 1A-1B, when embedding the magnetic material 14 in the distal tip 12 and/or the catheter 10, the magnetic material 14 may be covered or entirely surrounded by the wall, which may reduce contact of the magnetic material 14 with fluids flowing through the catheter 10. In some embodiments, the magnetic material 14 may include an annular ring, which may be embedded within the distal tip 12 of the catheter 10 and may provide predictable movement of the distal tip 12 in response to placement of the other magnetic material 26.

Figures 1C, 1D:
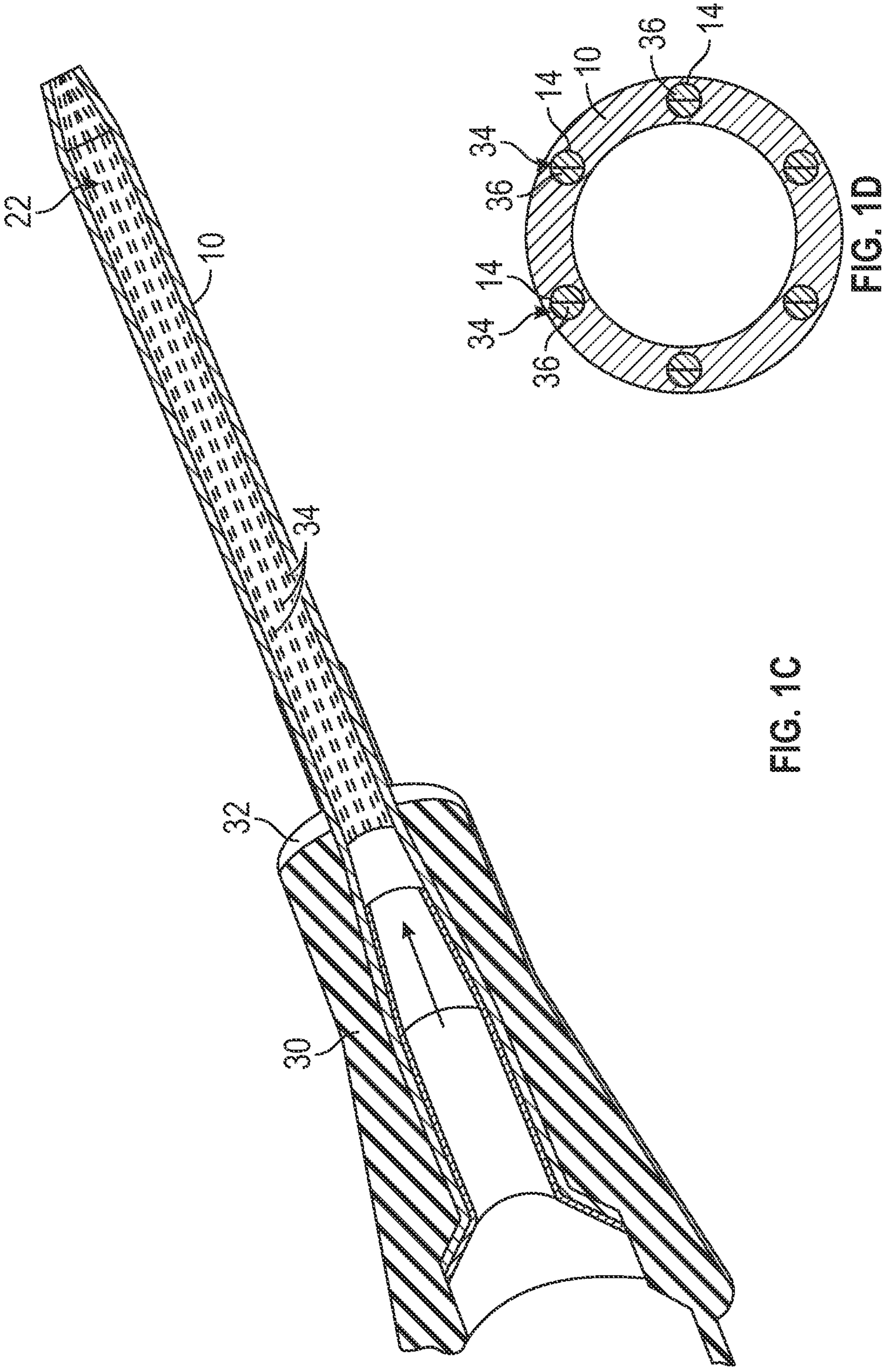
FIG. 1C is a longitudinal cross-sectional view of the catheter, illustrating example strips, according to some embodiments.
FIG. 1D is a transverse cross-sectional view of the catheter, illustrating the strips of FIG. 1C, according to some embodiments.

Referring now to FIGS. 1C-1D, in some embodiments, a catheter adapter 30 may include a distal end 32 in which the catheter 10 may be secured. In some embodiments, the catheter 10 may include one or more strips 34, which may extend longitudinally along the catheter 10. In some embodiments, the strips 34 may include a radiopaque material 36 and the magnetic material 14. In some embodiments, the radiopaque material 36 and the magnetic material 14 may be mixed together and/or co-extruded with the wall of the catheter 10. In some embodiments, the radiopaque material 36 and the magnetic material 14 may be disposed side by side within the strips 34, as illustrated, for example, in FIG. 1D.

In some embodiments, the radiopaque material 36 may facilitate visibility of the catheter 10 on x-ray film, and the magnetic material 14 may facilitate repositioning of the distal tip 12. In some embodiments, the strips 34 may extend from the distal tip 12 to the distal end 32, which may facilitate bending of a substantial length of the catheter 10 towards the other magnetic material 26 (the other magnetic material 26 is illustrated, for example, in FIG. 1B). In some embodiments, the strips 34 may terminate distal to the distal end 32 and/or may be limited to the distal tip 12, which may facilitate bending of the distal tip 12 towards the other magnetic material 26.

In some embodiments, the strips 34 may be embedded within a wall of the catheter 10. In some embodiments, when embedding the strips 34 within the wall of the catheter 10, portions of the strips 34 may be uncovered by the material of the wall. In other embodiments and as illustrated, for example, in FIGS. 1C-1D, when embedding the strips 34 within the wall of the catheter 10, the strips 34 may be covered or entirely surrounded by the wall, which may reduce contact of the magnetic material 14 and the radiopaque material 36 with fluids flowing through the catheter 10.

Figure 2A:
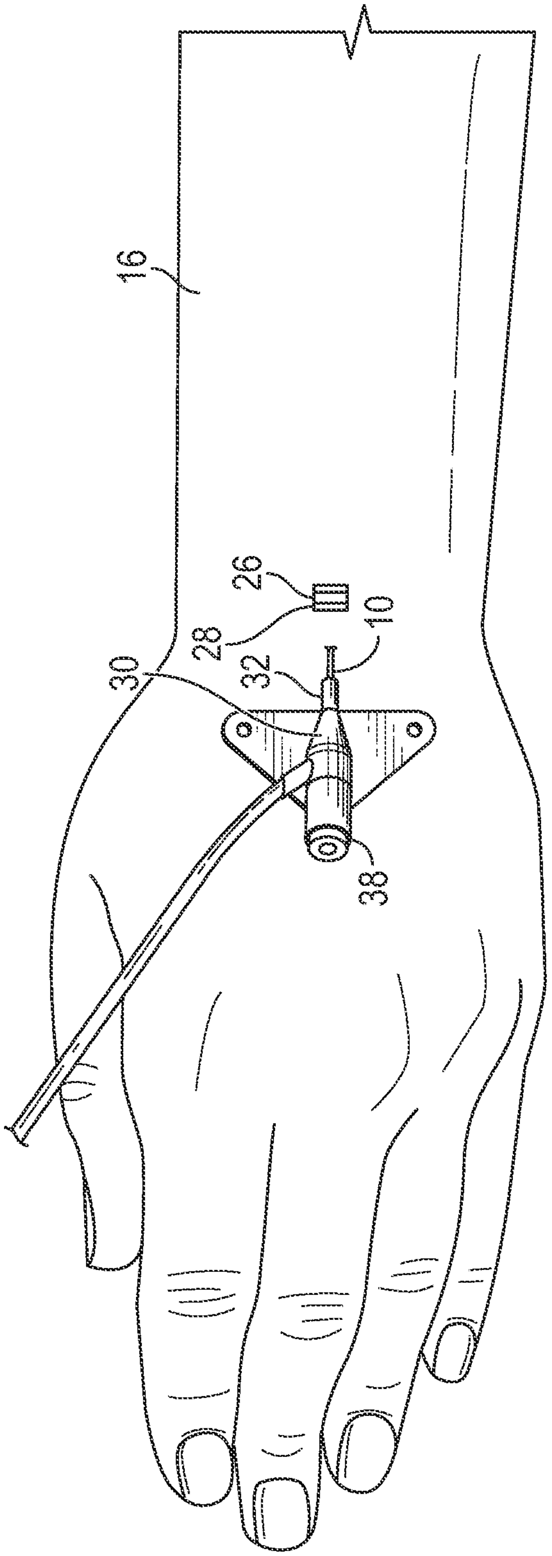
FIG. 2A is an upper perspective view of an example adhesive patch in a first location and an example catheter assembly, according to some embodiments.

Referring now to FIG. 2A, in some embodiments, the other magnetic material 26 may be generally aligned on the skin 16 with a longitudinal axis of the catheter 10, as illustrated, for example, in FIG. 2A. This may facilitate bending of the catheter 10 directly upwards towards the skin. In these embodiments, the other magnetic material 26 may be disposed directly above and covering the distal tip 12, which may enhance an attractive force between the magnetic material 14 and the other magnetic material 26, move the distal tip 12 away from the wall of the blood vessel, and reduce a risk of dislodgement of the catheter 10 due to the attractive force. In some embodiments, the distal tip 12 may include a distalmost portion of the catheter 10.

In some embodiments, a catheter assembly may include any suitable catheter assembly. In some embodiments, the catheter assembly may include an integrated catheter adapter, which may include a side port and an extension tube extending from the side port. In some embodiments, the catheter assembly may include a straight catheter adapter. In some embodiments, a catheter assembly may include the catheter adapter 30. In some embodiments, the catheter adapter 30 may include the distal end 32, a proximal end 38, and a lumen extending through the distal end 32 and the proximal end 38. In some embodiments, the catheter 10 may extend from the distal end 32 of the catheter adapter 30. In some embodiments, the catheter 10 may include a peripheral intravenous catheter, a midline catheter, a peripherally-inserted central catheter, or another catheter.

Figure 2B:
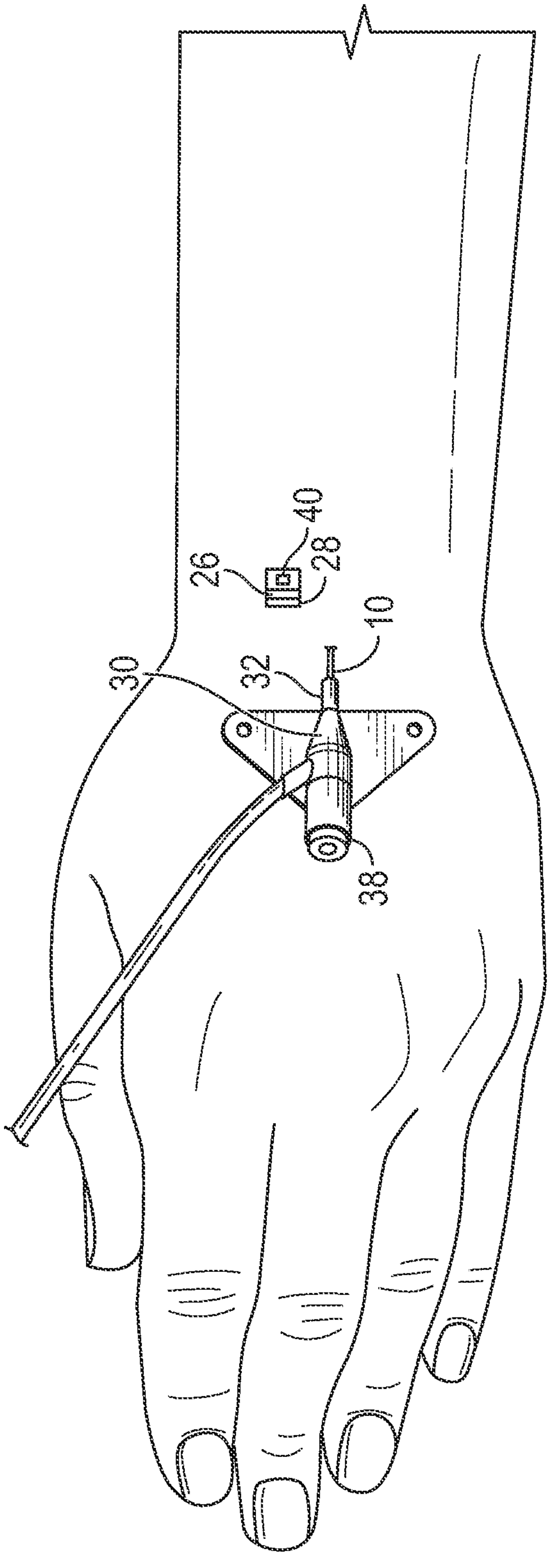
FIG. 2B is an upper perspective view of an example adhesive patch in a second location and the catheter assembly of FIG. 2A, according to some embodiments.

Referring now to FIG. 2B, in some embodiments, the other magnetic material 26 may be attached to the skin 16 to a side of the longitudinal axis of the catheter 10, as illustrated, for example, in FIG. 2B. This may facilitate upward movement of the distal tip 12 toward the skin 16, as well as side movement of the distal tip 12, which may facilitate movement of the distal tip 12 to a new location away from a particular thrombus. As illustrated in FIG. 2B, in some embodiments, the adhesive patch 28 may be coupled to a heating element 40, which may facilitate heating of the blood vessel 18 (see, for example, FIGS. 1A-1B), to increase blood flow, dilate the blood vessel, and ease blood draw.

Figure 3A:
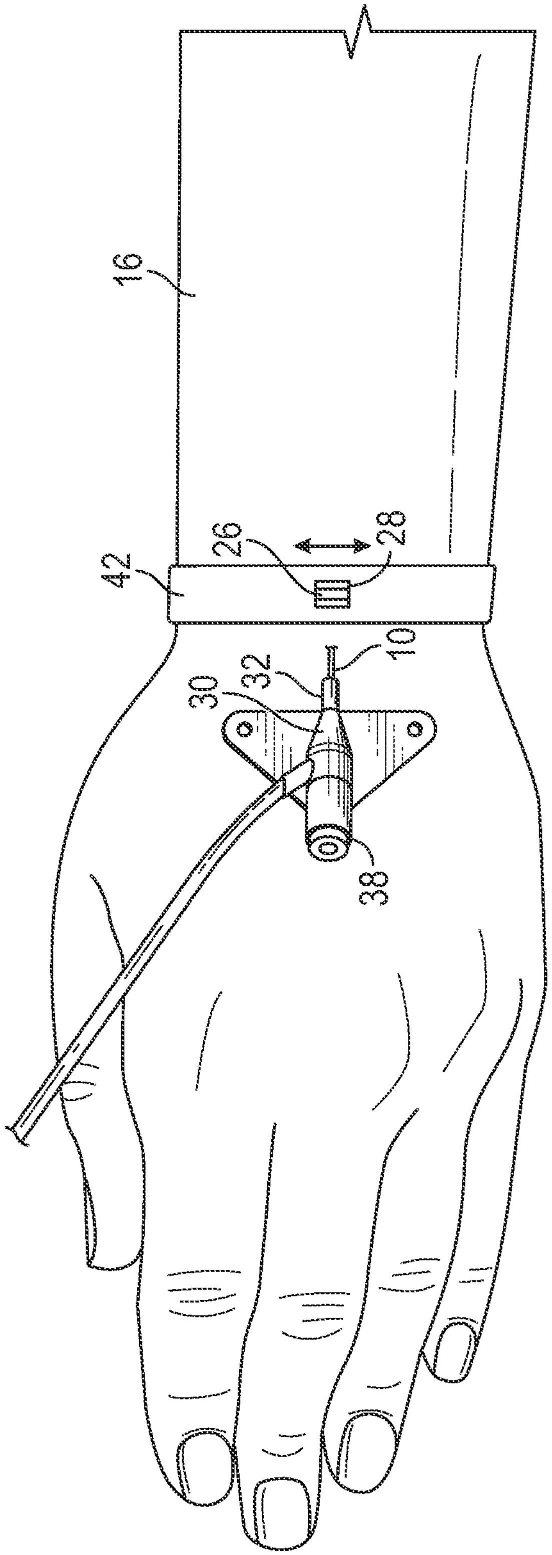
FIG. 3A is an upper perspective view of an example arm band and the catheter assembly of FIG. 2A, according to some embodiments.
Figure 3B:
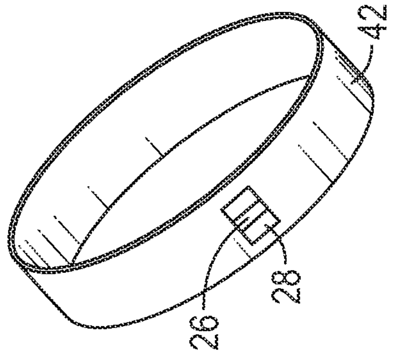
FIG. 3B is an upper perspective view of the arm band of FIG. 3A, according to some embodiments.

Referring now to FIGS. 3A-3B, in some embodiments, attaching the other magnetic material 26 to the skin 16 may include placing an arm band 42 around the skin 15. In some embodiments, the arm band 42 may be placed around the wrist, the forearm, the upper arm, or another suitable portion of an arm of a patient. In some embodiments, the arm band 42 may include a ring or a strip of material configured to form a ring around the arm via a clasp, buckle, tie, adhesive, VELCRO™, or other suitable coupling element.

In some embodiments, the other magnetic material 26 may be coupled to the arm band 42. In some embodiments, the arm band 42 may be rotated with respect to the skin 16 such that a position of the other magnetic material 26 is changed with respect to the distal tip 12. For example, the other magnetic material 26 may be aligned with the longitudinal axis of the catheter 10 or moved to a side of the longitudinal axis of the catheter 10. In some embodiments, the arm band 42 may be rotatably secured to the arm such that the other magnetic material 26 can be moved to different angular positions within the blood vessel until successful blood draw is enabled.

Figure 4:
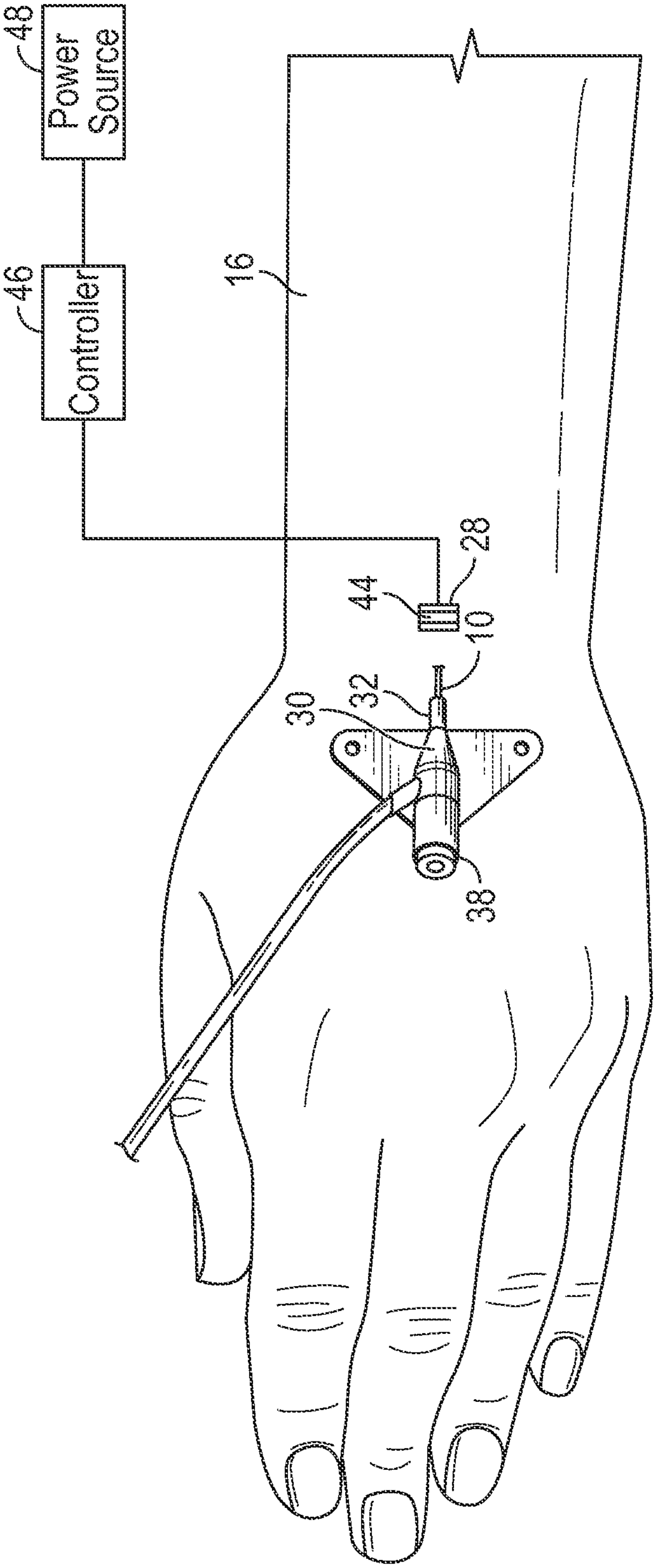
FIG. 4 is an upper perspective view of the catheter assembly of FIG. 2A and an example electromagnet, according to some embodiments.

Referring now to FIG. 4, the magnetic material 14 and/or the other magnetic material 26 may include an electromagnet 44. In some embodiments, the other magnetic material 26 may include the electromagnet 44, which may generate heat at the skin 16 that may pass to the blood vessel 18 to dilate the blood vessel 18 (see, for example, FIGS. 1A-1B) and increase blood flow therethrough. In some embodiments, the magnetic material 14 may include the electromagnet 44, which may facilitate heating of the catheter 10 through induction heating. In these embodiments, rapid heating of the catheter 10 via the electromagnet may dilate the blood vessel 18 and increase blood flow therethrough. In some embodiments, an electronic oscillator may be integrated into a control loop or controller 46, which may be operatively coupled to the electromagnet 44. In some embodiments, the controller 46 may be coupled to a power source 48.

Referring now to FIGS. 1-4, in some embodiments, a kit may include the catheter assembly and/or the other magnetic material 26. In some embodiments, the kit may include the adhesive patch 28, the arm band 42, or another means of attaching the other magnetic material 26 to the skin 16.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A method of repositioning a distal tip of a catheter for transfer of a fluid, the method comprising:

inserting a distal tip of a catheter of a catheter assembly into a blood vessel, wherein the distal tip of the catheter comprises a magnetic material;

attaching another magnetic material to skin, wherein the distal tip of the catheter moves towards the other magnetic material, wherein at least one of the magnetic material and the other magnetic material comprises a permanent magnet or an electromagnet, and wherein in moving the distal tip of the catheter towards the other magnetic material, the distal tip is separated away from a wall of the blood vessel or a thrombus formed in the blood vessel; and performing one of a blood draw or a fluid infusion via the catheter upon separation of the distal tip away from the wall of the blood vessel or the thrombus.

2. The method of claim 1, wherein the catheter assembly comprises a catheter adapter, wherein the catheter adapter comprises a distal end, a proximal end, and a lumen extending through the distal end and the proximal end, wherein the catheter extends from the distal end of the catheter adapter.

3. The method of claim 2, wherein the catheter comprises a peripheral intravenous catheter.

4. The method of claim 1, wherein attaching the other magnetic material to the skin comprises attaching an adhesive patch to the skin, wherein the other magnetic material is coupled to the adhesive patch.

5. The method of claim 4, wherein the adhesive patch is coupled to a heating element, the heating element heating the blood vessel above normal body temperature to dilate the blood vessel and increase blood flow.

6. The method of claim 1, wherein attaching the other magnetic material to the skin comprises placing an arm band around the skin, wherein the other magnetic material is coupled to the arm band.

7. The method of claim 6, further comprising rotating the arm band with respect to the skin such that a position of the other magnetic material is changed with respect to the distal tip.

8. The method of claim 1, wherein the other magnetic material is attached to the skin after the distal tip of the catheter of the catheter assembly is inserted into the blood vessel.

9. The method of claim 8, wherein the other magnetic material is attached to the skin such that the other magnetic material is aligned with a longitudinal axis of the catheter.

10. The method of claim 8, wherein the other magnetic material is attached to the skin at a side of a longitudinal axis of the catheter.

11. The method of claim 1, wherein the other magnetic material is attached to the skin before the distal tip of the catheter of the catheter assembly is inserted into the blood vessel, wherein the distal tip of the catheter of the catheter assembly is inserted into the blood vessel such that the other magnetic material is aligned with a longitudinal axis of the catheter or disposed to a side of the longitudinal axis of the catheter.

12. The method of claim 1, wherein the catheter comprises a plurality of strips extending longitudinally within the catheter and embedded within the catheter, wherein the strips comprise a radiopaque material and the magnetic material.

13. The method of claim 1, wherein the magnetic material is embedded in the distal tip of the catheter.

14. The method of claim 1, wherein the magnetic material comprises an annular ring embedded within the distal tip of the catheter.

* * * * *